United States Patent [19]

Rovnyak

[11] Patent Number: 4,555,579

[45] Date of Patent: Nov. 26, 1985

[54] DIOXOLENYLMETHYL ESTER PRODRUGS OF PHOSPHINIC ACID ACE INHIBITORS

[75] Inventor: George C. Rovnyak, Hopewell, N.J.

[73] Assignee: E. R. Squibb & Sons, Inc., Princeton, N.J.

[21] Appl. No.: 478,598

[22] Filed: Mar. 24, 1983

[51] Int. Cl.[4] ...................... C07F 9/65; A61K 31/675
[52] U.S. Cl. .................................... 548/409; 544/230; 544/243; 546/15; 546/22; 548/413; 548/112; 548/113
[58] Field of Search ............... 424/200; 548/413, 409, 548/112, 113; 546/22, 15; 544/243, 230; 514/86, 91, 89

[56] References Cited

U.S. PATENT DOCUMENTS

| | | | |
|---|---|---|---|
| 4,168,267 | 9/1979 | Petrillo | 548/413 |
| 4,337,201 | 6/1982 | Petrillo | 548/413 |
| 4,379,146 | 4/1983 | Greenlee et al. | 548/413 X |
| 4,427,665 | 1/1984 | Karanewsky et al. | 546/22 X |
| 4,432,971 | 2/1984 | Karanewsky et al. | 548/413 X |
| 4,448,772 | 5/1984 | Karanewsky | 546/22 |
| 4,452,791 | 6/1984 | Ryono et al. | 548/409 X |

FOREIGN PATENT DOCUMENTS

| | | |
|---|---|---|
| 0039477 | 11/1981 | European Pat. Off. |
| 0039086 | 11/1981 | European Pat. Off. |
| 0058427 | 8/1982 | European Pat. Off. |

OTHER PUBLICATIONS

Brietbeil et al., Trans. Ill. State Acad. Sci., 67:139–144, (1974).
Ehrenfreund et al., Tetrahedron, vol. 28, pp. 1697–1704, (1972).
Fischler, et al., Tetrahedron Letters, No. 17, pp. 1701–1704, (1972).
Sakamoto, et al., Chemical Abstracts, vol. 98, 143,458q (1982).
Christensen, et al., Chemical Abstracts, vol. 99, 10851m (1983), abstract of Eur. Pat. Appl. EP 70,013, 01/19/83.

Primary Examiner—Donald G. Daus
Assistant Examiner—D. G. Rivers
Attorney, Agent, or Firm—Lawrence S. Levinson; Donald J. Barrack

[57] ABSTRACT

Angiotensin converted enzyme inhibitor activity if exhibited by compounds having the formula

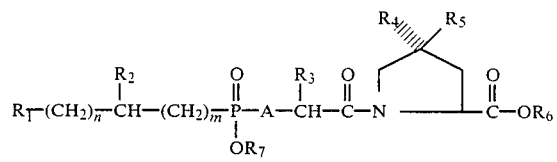

and salts thereof wherein $R_1$ is hydrogen, aryl, or heteroaryl;

$R_2$ is hydrogen, amino, alkanoylamino, arylcarbonylamino, or heteroarylcarbonylamino;

$R_3$ is hydrogen, alkyl, or aminoalkyl;

$R_4$ and $R_5$ are the same or different and each is hydrogen, alkyl, halogen, aryl, arylalkyl, hydroxy, alkoxy, alkylthio, aryloxy, arylthio, or cycloalkyl, or $R_4$ and $R_5$ taken together are oxo, ethylenedithio or propylenedithio;

one of $R_6$ and $R_7$ is

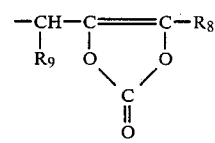

and the other is hydrogen, alkyl or arylalkyl;

$R_8$ is hydrogen, alkl or aryl;

$R_9$ is hydrogen or alkyl;

n is 0 or an integer of 1 to 8;

m is 0 or 1; and

A is $-(CH_2)_p-$ wherein p is 0 or 1, $-NH-$, or $-O-$.

9 Claims, No Drawings

DIOXOLENYLMETHYL ESTER PRODRUGS OF PHOSPHINIC ACID ACE INHIBITORS

BACKGROUND OF THE INVENTION

The recent literature discloses a variety of mercaptoacyl amino acids which are useful for inhibiting the conversion of angiotensin I to angiotensin II, and are therefore useful in the treatment of hypertension.

U.S. Pat. Nos. 4,168,267, issued Sept. 18, 1979 and 4,337,201, issued June 29, 1982 disclose phosphinylalkanoyl prolines and esters and salts thereof. These compounds are inhibitors of the action of angiotensin converting enzyme in mammals and are hypotensive agents.

BRIEF DESCRIPTION OF THE INVENTION

Compounds having the formula $$R_1-(CH_2)_n-\underset{R_2}{CH}-(CH_2)_m-\underset{\underset{OR_7}{|}}{\overset{O}{\overset{\|}{P}}}-A-\underset{R_3}{CH}-\overset{O}{\overset{\|}{C}}-N\underbrace{\qquad}_{R_4\;R_5}\overset{O}{\overset{\|}{C}}-OR_6$$

and salts thereof, have hypotensive activity. In formula I, and throughout the specification, the symbols are as defined below.

$R_1$ is hydrogen, aryl, or heteroaryl;

$R_2$ is hydrogen, amino, alkanoylamino, arylcarbonylamino, or heteroarylcarbonylamino;

$R_3$ is hydrogen, alkyl, or aminoalkyl;

$R_4$ and $R_5$ are the same or different and each is hydrogen, alkyl, halogen, aryl, arylalkyl, hydroxy, alkoxy, alkylthio, aryloxy, arylthio, or cycloalkyl, or $R_4$ and $R_5$ taken together are oxo (=O), ethylenedithio or propylenedithio;

one of $R_6$ and $R_7$ is $$-\underset{R_9}{\overset{|}{CH}}-\underset{O}{\overset{|}{C}}\underset{\underset{\underset{O}{\|}}{C}}{=}\underset{O}{\overset{|}{C}}-R_8$$

and the other is hydrogen, alkyl or arylalkyl;

$R_8$ is hydrogen, alkyl or aryl;

$R_9$ is hydrogen or alkyl;

n is 0 or an integer of 1 to 8;

m is 0 or 1; and

A is $-(CH_2)_p-$ wherein p is 0 or 1, $-NH-$, or $-O-$.

The term "aryl", as used throughout the specification either by itself or as part of a larger group, refers to phenyl or phenyl substituted with halogen, alkyl, alkoxy, alkylthio, hydroxy, alkanoyl, nitro, amino, dialkylamino, or trifluoromethyl groups. Phenyl and monosubstituted phenyl are preferred.

The term "alkyl", as used throughout the specification either by itself or as part of a larger group, refers to groups having 1 to 10 carbon atoms. Alkyl groups having 1 to 4 carbon atoms are preferred.

The term "alkoxy", as used throughout the specification either by itself or as part of a larger group, refers to groups having 1 to 8 carbon atoms. Alkoxy groups having 1 to 3 carbon atoms are preferred.

The term "halogen", as used throughout the specification either by itself or as part of a larger group, refers to fluorine, chlorine, bromine and iodine. The preferred halogen groups are fluorine and chlorine.

The term "alkanoyl", as used throughout the specification either by itself or as part of a larger group, refers to groups having 2 to 10 carbon atoms.

The term "heteroaryl", as used throughout the specification, either by itself or as part of a larger group, refers to pyridyl, furyl, thienyl, pyrimidinyl, quinolyl, indolyl, benzothiophenyl, benzothiazolyl, purinyl, benzoxazolyl, and thiazolyl.

DETAILED DESCRIPTION OF THE INVENTION

The compounds of formula I, and salts thereof, are hypotensive agents. They inhibit the conversion of the decapeptide angiotensin I to angiotensin II and, therefore, are useful in reducing or relieving angiotensin related hypertension. The action of the enzyme renin or angiotensinogen, a pseudoglobulin in blood plasma, produces angiotensin I. Angiotensin I is converted by angiotensin converting enzyme (ACE) to angiotensin II. The latter is an active pressor substance which has been implicated as the causative agent in several forms of hypertension in various mammalian species, e.g., humans. The compounds of this invention intervene in the angiotensinogen (renin) angiotensin I (ACE) angiotensin II sequence by inhibiting angiotensin converting enzyme and reducing or eliminating the formation of the pressor substance angiotensin II. Thus by the administration of a composition containing one (or a combination) of the compounds of this invention, angiotensin dependent hypertension in a species of mammal (e.g., humans) suffering therefrom is alleviated. A single dose, or preferably two to four divided daily doses, provided on a basis of about 0.1 to 100 mg. per kilogram of body weight per day, preferably about 1 to 15 mg. per kilogram of body weight per day is appropriate to reduce blood pressure. The substance is preferably administered orally, but parenteral routes such as the subcutaneous, intramuscular, intravenous or intraperitoneal routes can also be employed.

The compounds of this invention can also be formulated in combination with a diuretic for the treatment of hypertension. A combination product comprising a compound of this invention and a diuretic can be administered in an effective amount which comprises a total daily dosage of about 30 to 600 mg., preferably about 30 to 330 mg. of a compound of this invention, and about 15 to 300 mg., preferably about 15 to 200 mg. of the diuretic, to a mammalian species in need thereof. Exemplary of the diuretics contemplated for use in combination with a peptide of this invention are the thiazide diuretics, e.g., chlorthiazide, hydrochlorthiazide, flumethiazide, hydroflumethiazide, bendroflumethiazide, methychlothiazide, trichlormethiazide, polythiazide or benzthiazide as well as ethacrynic acid, ticrynafen, chlorthalidone, furosemide, musolimine, bumetanide, triamterene, amiloride and spironolactone and salts of such compounds.

The compounds of formula I can be formulated for use in the reduction of blood pressure in compositions such as tablets, capsules or elixirs for oral administration, or in sterile solutions or suspensions for parenteral administration. About 10 to 500 mg. of a compound of formula I is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

The compounds of this invention wherein $R_7$ is

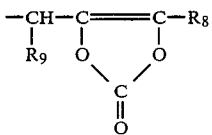

can be prepared from the corresponding compound having the formula II

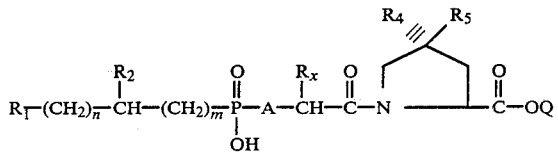

wherein Q is an acid labile carboxyl protecting group and $R_x$ is hydrogen, alkyl or (protected amino) alkyl. Exemplary "Q" groups are benzhydryl and t-butyl groups. The protecting group of the (protected amino)alkyl substituent is preferably an acid labile group.

A compound of formula II can be alkylated with a dioxolenylmethyl halide having the formula III

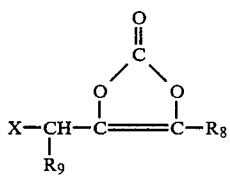

wherein X is a halogen, preferably bromine or chlorine. The alkylation reaction will preferably take place in the presence of a tertiary amine (e.g., triethylamine), in a polar aprotic solvent (e.g., dimethylformamide and dimethylsulfoxide). It is preferred that the dioxolenylmethyl halide of formula III and the tertiary amine each be present in an amount of about 1 to 1.5 equivalents of the protected phosphinylalkanoyl amino acid. The reaction temperature will preferably be about 0° to 50° C. The resulting compound can be deprotected under acidic conditions using art recognized techniques to give the compounds of this invention, wherein $R_6$ is hydrogen.

Alternatively, the products of formula I wherein $R_7$ is

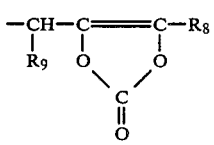

can be prepared by forming a tetraalkylammonium salt of the protected compound of formula II and reacting this salt with about 1 to 1.5 equivalents of a dioxolenylmethyl halide of formula III in the presence of a small amount (preferably about 0.2 equivalents) of a tertiary amine. The reaction is preferably run in a non-polar aprotic solvent such as a halogenated hydrocarbon (e.g., dichloromethane) at a temperature of from about ambient temperature to reflux temperature. Deprotection under acidic conditions yields the desired product wherein $R_6$ is hydrogen.

Those products of formula I wherein $R_6$ is alkyl or arylalkyl are readily obtainable by alkylation of the corresponding free acid of formula I (i.e., $R_6$ is hydrogen).

The compounds of this invention wherein $R_6$ is

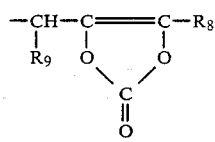

can be prepared by coupling a compound having the formula IV

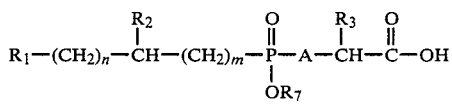

with a compound having the formula V

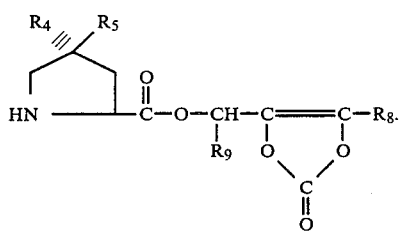

The coupling can be accomplished using known amide bond forming procedures. For example, the reaction can be run in the presence of a coupling reagent such as dicycohexylcarbodiimide, or the acid of formula IV can be activated by formation of its mixed anhydride, symmetrical anhydride, acid halide (preferably acid chloride) or acid ester, or by use of Woodward reagent K, N-ethoxycarbonyl-2-ethoxy-1,2-dihydroquinoline, N,N'-carbonyldiimidazole or the like. A review of these methods can be found in *Methoden der Organischen Chemie* (Houben-Weyl), Vol. XV, part III, page 1 et seq. (1974).

Those products of formula I wherein $R_7$ is hydrogen are also obtainable by treatment of the corresponding product wherein $R_7$ is alkyl or arylalkyl with trimethylsilylbromide.

Those products of formula I wherein $R_6$ or $R_7$ is hydrogen form basic salts with various inorganic and organic bases which are also within the scope of the invention. Such salts include ammonium salts, alkali metal salts such as lithium, sodium and potassium salts (which are preferred), alkaline earth metal salts such as the calcium and magnesium salts, salts with organic bases, e.g., dicyclohexylamine salt, benzathine, N-methyl-D-glucamine, hydrabamine salts, salts with amino acids like arginine, lysine and the like. The nontoxic, physiologically acceptable salts are preferred, although other salts are also useful, e.g., in isolating or purifying the product. The salts are formed using conventional techniques.

The dioxolenylmethyl halides of formula III can be prepared using the methodology described in European Patent Application No. 0039477, published Nov. 11, 1981, European Patent Application No. 0039086, published Nov. 4, 1981, *Trans. Ill. State Acad. Sci.*, 67:139 (1974), and *Tet. Let.*, 1701 (1972).

The phosphinylalkanoyl prolines of formula II wherein A is $-(CH_2)_p-$, p is 0 or 1, and $R_x$ is hydrogen or alkyl can be prepared using the methodology described in U.S. Pat. No. 4,337,201, issued June 29, 1982.

The phosphinylalkanoyl prolines of formula II wherein A is $-(CH_2)_p-$, p is 0 or 1 and $R_x$ is (protected amino)alkyl can be prepared using the methodology described in U.S. patent appliation Ser. No. 357,941, filed Mar. 15, 1982, now U.S. Pat. No. 4,452,791, issued June 5, 1984, the disclosure of which is incorporated herein.

Treating an acrylate ester having the formula VI $$CH_2=\overset{R_x}{\underset{}{C}}-\overset{O}{\underset{}{\overset{\|}{C}}}-O-CH_3$$

with the appropriate diester having the formula VII $$R_1-(CH_2)_n-\overset{R_2}{\underset{}{CH}}-(CH_2)_m-\overset{O}{\underset{}{\overset{\|}{P}}}-(O-alkyl)_2$$

produces the corresponding Michael adduct having the formula VIII $$R_1-(CH_2)_n-\overset{R_2}{\underset{}{CH}}-(CH_2)_m-\overset{O}{\underset{O-alkyl}{\overset{\|}{P}}}-CH_2-\overset{R_x}{\underset{}{CH}}-\overset{O}{\underset{}{\overset{\|}{C}}}-O-CH_3$$

Compounds of formula II wherein A is $-(CH_2)_p-$, p is 1 and $R_x$ is (protected amino)alkyl are obtained by saponification of a compound of formula VIII, followed by coupling with the appropriate amino acid having the formula IX $$HN\underset{}{\overset{R_4\quad R_5}{\diagup\!\!\!\diagdown}}\overset{O}{\underset{}{\overset{\|}{C}}}-OQ.$$

yielding a compound having the formula X $$R_1-(CH_2)_n-\overset{R_2}{\underset{}{CH}}-(CH_2)_m-\overset{O}{\underset{O-alkyl}{\overset{\|}{P}}}-A-\overset{R_x}{\underset{}{CH}}-\overset{O}{\underset{}{\overset{\|}{C}}}-N\underset{}{\overset{R_4\quad R_5}{\diagup\!\!\!\diagdown}}\overset{O}{\underset{}{\overset{\|}{C}}}-OQ.$$

The coupling can be accomplished using known amide bond forming procedures as described above. The desired starting material of formula II (A is $-(CH_2)_p-$, p is 1 and $R_x$ is (protected amino)alkyl) can then be obtained by removal of the phosphinylalkyl ester with trimethylsilylbromide.

Compounds of formula II wherein A is $-(CH_2)_p-$, p is 1 and $R_x$ is (protected amino)alkyl are obtained by coupling a phosphinylacetic acid (or its activated form) having the formula XI $$R_1-(CH_2)_n-\overset{R_2}{\underset{}{CH}}-(CH_2)_m-\overset{O}{\underset{O-alkyl}{\overset{\|}{P}}}-A-\overset{R_x}{\underset{}{CH}}-\overset{O}{\underset{}{\overset{\|}{C}}}-OH$$

with the appropriate imino acid of formula IX and is accomplished using known amide bond forming procedures as described above. The desired starting material of formula II (A is $-(CH_2)_p-$, p is 0 and $R_x$ is (protected amino)alkyl) can be obtained by removal of the phosphinylalkyl ester with trimethylsilylbromide.

The proline derivatives of formula II wherein A is oxygen can be prepared utilizing the methodology described in U.S. patent application No. 391,884, filed June 23, 1982, now U.S. Pat. No. 4,452,790, issued June 5, 1984, the disclosure of which is incorporated herein.

A phosphinic acid having the formula XIII $$R_1-(CH_2)_n-\overset{R_2}{\underset{}{CH}}-(CH_2)_m-\overset{O}{\underset{OH}{\overset{\|}{P}}}-OH$$

can be treated with a chlorinating agent such as phosphorus pentachloride in the presence of an inert organic solvent such as benzene to form a compound of the formula XIV $$R_1-(CH_2)_n-\overset{R_2}{\underset{}{CH}}-(CH_2)_m-\overset{O}{\underset{Cl}{\overset{\|}{P}}}-Cl$$

A compound of formula XIII can be reacted with a lactate having the formula XV $$HO-\overset{R_x}{\underset{}{CH}}-\overset{O}{\underset{}{\overset{\|}{C}}}-O-alkyl$$

in the presence of an organic base such as triethylamine followed by an alcohol Z—OH (wherein Z is alkyl, benzyl or benzhydryl) to form a compound having the formula XV $$R_1-(CH_2)_n-\overset{R_2}{\underset{}{CH}}-(CH_2)_m-\overset{O}{\underset{OZ}{\overset{\|}{P}}}-O-\overset{R_x}{\underset{}{CH}}-\overset{O}{\underset{}{\overset{\|}{C}}}-O-alkyl.$$

Treatment of a compound of formula XV with strong base such as sodium hydroxide or lithium hydroxide in a mixture of water and an organic solvent such as dioxane yields the corresponding acid having the formula XVI $$R_1-(CH_2)_n-\overset{R_2}{\underset{}{CH}}-(CH_2)_m-\overset{O}{\underset{OZ}{\overset{\|}{P}}}-O-\overset{R_x}{\underset{}{CH}}-\overset{O}{\underset{}{\overset{\|}{C}}}-OH.$$

The acid of formula XVI (or its activated form) is then coupled with an imino acid of formula X and the Z protecting group removed to yield the desired starting material of formula II wherein A is oxygen.

The proline derivatives of formula II wherein A is NH can be prepared using the methodology described in European Patent Application No. 0058427, published Aug. 25, 1982.

The preferred compounds of this invention are those compounds of formula I wherein $R_1$ is phenyl, $R_2$ is hydrogen or benzoylamino, n is 2, m is 1, A is —(CH$_2$)$_p$—, $R_4$ and $R_5$ are the same or different and each is hydrogen, alkyl, cycloalkyl, or phenylthio, or $R_4$ and $R_5$ taken together are ethylenedithio, one of $R_6$ and $R_7$ is hydrogen and the other is

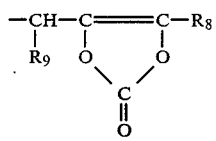

wherein $R_8$ is hydrogen, alkyl or phenyl.

The following examples are specific embodiments of this invention.

EXAMPLE 1

(S)-7-[[[(2-Oxo-5-phenyl-1,3-dioxol-4-yl)methoxy](4-phenylbutyl)phosphinyl]acetyl]-1,4-dithia-7-azaspiro[4.4]nonane-8-carboxylic acid (A)

(S)-7-[[[(2-Oxo-5-phenyl-1,3-dioxol-4-yl)methoxy](4-phenylbutyl)phosphinyl]acetyl]-1,4-dithia-7-azaspiro[4.4]nonane-8-carboxylic acid, diphenylmethyl ester Equimolar amounts of (S)-7-[[hydroxy(4-phenylbutyl)phosphinyl]acetyl]-1,4-dithia-7-azaspiro[4.4]nonane-8-carboxylic acid, diphenylmethyl ester and tetra-n-butylammonium sulfate were shaken in dichloromethane/water containing two equivalents of lithium hydroxide. Drying the organic fraction by toluene azeotrope yielded (S)-7-[[(hydroxy(4-phenylbutyl)phosphinyl]acetyl]-1,4-dithia-7-azaspiro[4.4]nonane-8-carboxylic acid, diphenylmethylester, tetra-n-butylammonium salt.

A solution of the above salt (2.5 g, 2.93 mmole) in 30 ml of chloroform (over aluminum oxide) under argon at room temperature was treated with triethylamine (0.05 ml) and 4-bromomethyl-5-phenyl-1,3-dioxol-2-one (936 mg, 3.67 mmole). After heating at reflux temperature for 4.5 hours, solvent was removed in vacuo. The residue was dissolved in ethyl acetate, washed with 10% potassium bisulfate, water, and saturated brine (twice); the aqueous fractions were dried over magnesium sulfate and concentrated in vacuo yielding 2.4 g of the title compound. Flash chromatography on 800 ml of silica gel and elution with ethyl acetate/hexane (2 liters of 1:1, 2 liters of 3:1 and 2 liters of 1:0) gave 0.94 g of the title compound as a homogenous product: thin layer chromatography, silica gel, ethyl acetate. $R_f$=0.59.

Anal.: Cal'd C$_{42}$H$_{42}$NO$_8$PS$_2$.0.37H$_2$O): C, 63.80; H, 5.60; N, 1.77; P, 3.92; S, 8.11; Found: C, 63.80; H, 5.67; N, 2.22; P, 3.9; S, 7.83.

(B)

(S)-7-[[[(2-Oxo-5-phenyl-1,3-dioxo-4-yl)methoxy](4-phenylbutyl)phosphinyl]acetyl]1,4-dithia-7-azaspiro[4.4]nonane-8-carboxylic acid (S)-7-[[[(2-Oxo-5-phenyl-1,3-dioxol-4-yl)methoxy](4-phenylbutyl)phosphinyl]acetyl]1,4-dithia-7-azaspiro[4.4]nonane-8-carboxylic acid, diphenylmethyl ester (1.28 g, 1.6 mmole) in 20 ml of dichloromethane was cooled to 0°–5° C. under argon and treated with 1.2 ml of trifluoroacetic acid and 0.3 ml of anisole. After 2 hours, solvent and excess reagent were removed in vacuo and the residue, dissolved in ethyl acetate, was washed with water and saturated brine; the aqueous fractions were backwashed with fresh ethyl acetate. The combined organic fractions were dried over magnesium sulfate and concentrated in vacuo to give 1.85 g of an oil. Flash chromatography on 300 ml of silica gel and elution with 2 liters of dichloromethane/methanol/acetic acid (40:1:1) gave 900 mg of homogenous product as a foam; thin layer chromatography, silica gel, dichloromethane/methanol/acetic acid, $R_f$=0.45.

Anal.: Calc'd C$_{29}$H$_{32}$NO$_8$PS$_2$: C, 55.58; H, 5.31; N, 2.24; P, 4.94; S, 10.23; Found: C, 55.66; H, 5.11; N 2.12; P, 4.8; S, 10.25.

What is claimed is:

1. A compound having the formula

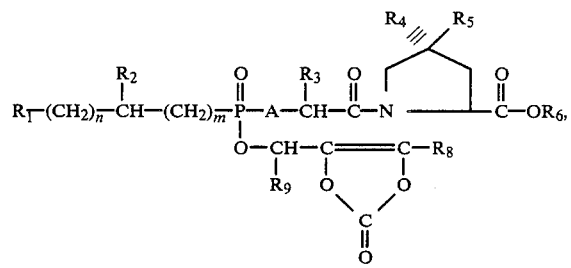

or a salt thereof, wherein $R_1$ is hydrogen, aryl or heteroaryl;

$R_2$ is hydrogen, amino, alkanoylamino, arylcarbonylamino, or heteroarylcarbonylamino;

$R_3$ is hydrogen, alkyl, or aminoalkyl, $R_4$ and $R_5$ are the same or different and each is hydrogen, alkyl, halogen, aryl, arylalkyl, hydroxy, alkoxy, alkylthio, aryloxy, arylthio, or cycloalkyl, or $R_4$ and $R_5$ taken together are oxo, ethylenedithio or propylenedithio;

$R_6$ is hydrogen, alkyl or aryl;

$R_8$ is hydrogen, alkyl or aryl;

$R_9$ is hydrogen or alkyl;

n is 0 or an integer of 1 to 8;

m is 0 or 1; and

A is —(CH$_2$)$_p$— wherein p is 0 or 1, —NH—, or —O—;

wherein the term "aryl" refers to phenyl or phenyl substituted with halogen, alkyl, alkoxy, alkylthio, hydroxy, alkanoyl, nitro, amino, dialkylamino, or trifluoromethyl groups;

the term "alkyl" refers to groups having 1 to 10 carbon atoms;

the term "alkoxy" refers to groups having 1 to 8 carbon atoms;

the term "alkanoyl" refers to groups having 2 to 10 carbon atoms; and the term "heteroaryl" refers to pyridyl, furyl, thienyl, pyrimidinyl, quinolyl, indolyl, benzothiophenyl, benzothiazolyl, purinyl, benzoxazolyl, or thiazolyl.

2. A compound in accordance with claim 1 wherein $R_1$ is phenyl.

3. A compound in accordance with claim 1 wherein $R_2$ is hydrogen or benzoylcarbonylamino.

4. A compound in accordance with claim 1 wherein n is 2 and m is 1.

5. A compound in accordance with claim 1 wherein A is $-(CH_2)_p-$.

6. A compound in accordance with claim 1 wherein $R_4$ and $R_5$ are the same or different and each is hydrogen, alkyl, cycloalkyl, or phenylthio, or $R_4$ and $R_5$ taken together are ethylenedithio.

7. A compound in accordance with claim 1 wherein $R_8$ is hydrogen, alkyl or phenyl.

8. A compound in accordance with claim 1 wherein $R_1$ is phenyl; $R_2$ is hydrogen or benzoylamino; n is 2, m is 1; A is $-(CH_2)_p-$; $R_4$ and $R_5$ are the same or different and each is hydrogen, alkyl, cycloalkyl or phenylthio; or $R_4$ and $R_5$ taken together are ethylenedithio; and $R_8$ is hydrogen, alkyl or phenyl.

9. The compound in accordance with claim 1, (S)-7-[[[(2-oxo-5-phenyl-1,3-dioxol-4-yl)methoxy](4-phenylbutyl)phosphinyl]acetyl]-1,4-dithia-7-azaspiro[4.4]nonane-8-carboxylic acid.

* * * * *